(12) United States Patent
De La Rosa

(10) Patent No.: US 6,623,118 B2
(45) Date of Patent: Sep. 23, 2003

(54) STIMULUS AND METHOD FOR MEASURING THE FIELD OF VISION OF THE HUMAN EYE

(75) Inventor: Manuel Gonzalez De La Rosa, Santa Cruz de Tenerife (ES)

(73) Assignee: Interzeag AG (CH)

( * ) Notice: Subject to any disclaimer, the term of this patent is extended or adjusted under 35 U.S.C. 154(b) by 28 days.

(21) Appl. No.: 09/836,446

(22) Filed: Apr. 17, 2001

(65) Prior Publication Data

US 2002/0047996 A1 Apr. 25, 2002

(30) Foreign Application Priority Data

Apr. 18, 2000 (CH) .............................. 0773/00

(51) Int. Cl.$^7$ ............................................. A61B 3/02
(52) U.S. Cl. ................................................ 351/224
(58) Field of Search .................... 351/222, 223, 351/224, 237, 239, 243, 246

(56) References Cited

U.S. PATENT DOCUMENTS

| | | | | |
|---|---|---|---|---|
| 4,526,452 A | * | 7/1985 | Hirsch | 351/243 |
| 4,765,732 A | * | 8/1988 | Enoch | 351/243 |
| 4,822,162 A | * | 4/1989 | Richardson et al. | 351/243 |
| 5,223,865 A | * | 6/1993 | Shirao et al. | 351/243 |
| 5,539,482 A | * | 7/1996 | James et al. | 351/246 |
| 5,550,602 A | * | 8/1996 | Braeuning | 351/246 |
| 5,912,723 A | * | 6/1999 | Maddess | 351/246 |
| 5,946,075 A | * | 8/1999 | Horn | 351/246 |
| 6,027,217 A | * | 2/2000 | McClure et al. | 351/224 |
| 6,033,076 A | * | 3/2000 | Braeuning et al. | 351/224 |
| 6,227,668 B1 | * | 5/2001 | McKinnon et al. | 351/222 |
| 6,260,970 B1 | * | 7/2001 | Horn | 351/246 |
| 6,386,706 B1 | * | 5/2002 | McClure et al. | 351/237 |

OTHER PUBLICATIONS

Comparison of conventional and high–pass resolution perimetry in a prospective study of patients with glaucoma and healthy controls.; Chauhan BC; Archives of Ophthalmology [NLM—Medline]; Jan. 1999; vol. 117, Iss. 1; p. 2.*
Temporal contrast sensitivity with peripheral and central stimulation in glaucoma diagnosis; Isabel M Velten; British Journal of Ophthalmology, London; Feb. 1999; vol. 83, Iss. 2; p. 199, 7 pgs.*

* cited by examiner

Primary Examiner—Marvin M. Lateef
Assistant Examiner—John R. Sanders
(74) Attorney, Agent, or Firm—Webb Ziesenheim Logsdon Orkin & Hanson, P.C.

(57) ABSTRACT

A device and method for providing a stimulus to the measurement of the field of vision of the human eye. The stimulus is presented at predetermined test sites in a region of the background of a perimeter to a person to be tested. The stimulus has at least two visual characteristics that can be varied for the determination of a threshold. The stimulus is preferably formed by sine waves.

11 Claims, 1 Drawing Sheet

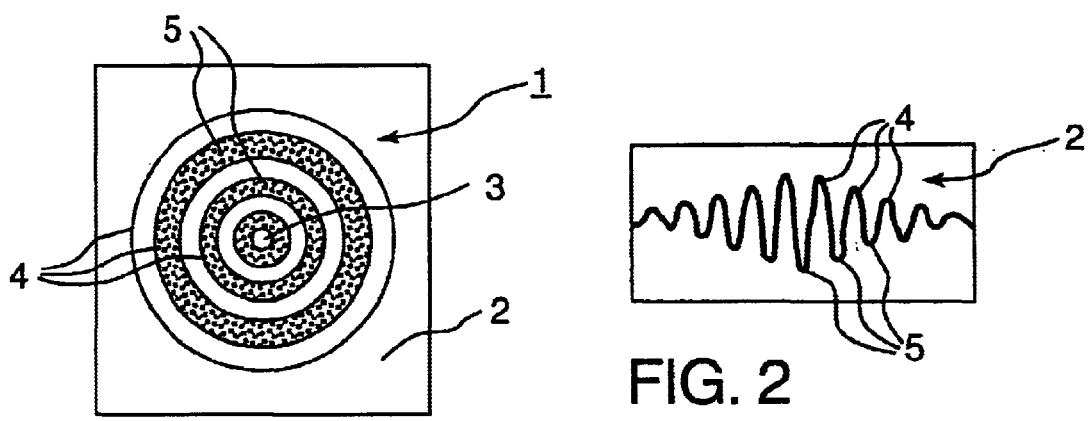
FIG. 1
FIG. 2
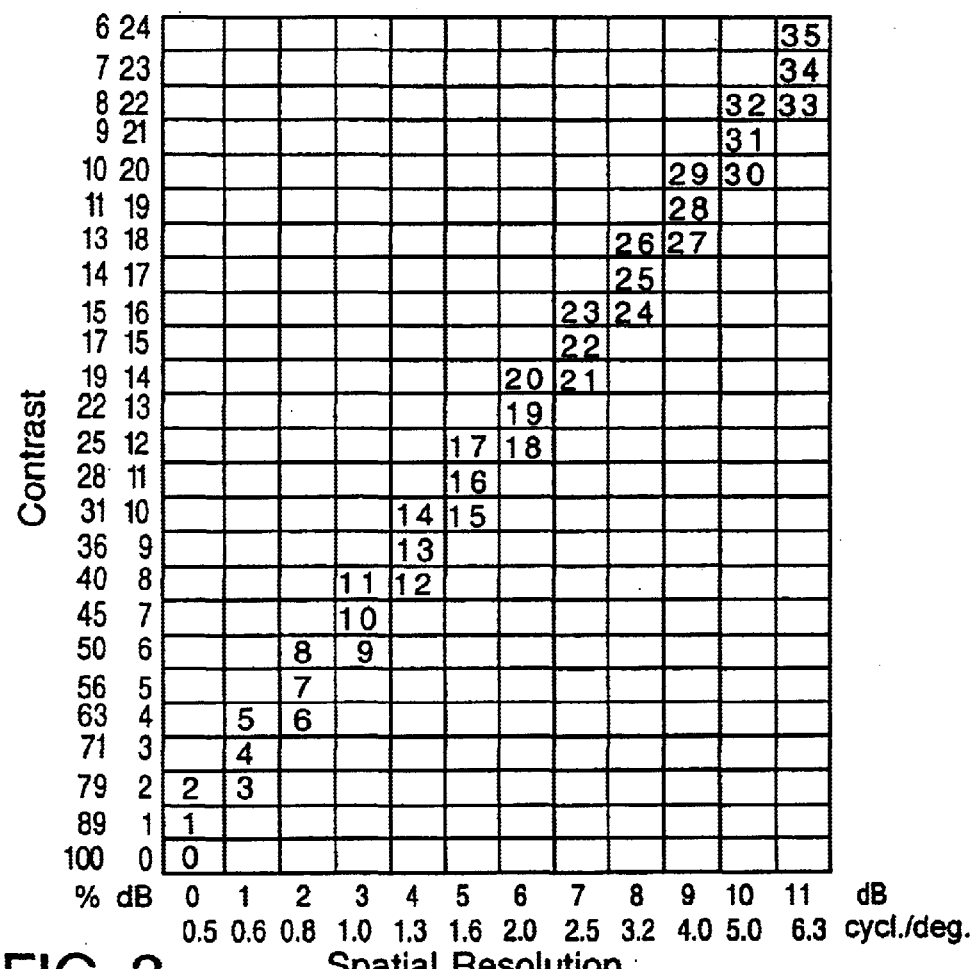
FIG. 3

STIMULUS AND METHOD FOR MEASURING THE FIELD OF VISION OF THE HUMAN EYE

FIELD OF THE INVENTION

This invention relates to a stimulus for measuring the field of vision of the human eye which is presented to a test subject as a region of the background of a perimeter.

DESCRIPTION OF THE RELATED ART

In perimetry measurement, stimuli are used in particular for the early detection of disorders and also for the observation of the changes in said disorders. The stimuli are presented for relatively short periods of time in defined points of the field of vision. The stimuli of the prior art are points of light that appear for brief periods on the surface of the perimeter. Thresholds can be determined by varying the luminance. The stimuli used for this purpose are presented at different luminous intensities and the test subject is required to push a response button when the stimulus is perceived. The stimulus is displayed at predetermined test locations with greater and lesser intensity so that a sensitivity threshold is exceeded one or more times. The threshold is a stimulus intensity (in decibels) at which, after a certain number of presentations, 50% of the presentations are seen. With the stimuli of the prior art, therefore, only the luminance is varied.

An important perimeter test method is used for the early detection of glaucoma. The essential feature is the selective recognition of magnocellular fibers. The detection of such fibers can be used for the early detection of glaucoma. Magnocellular systems have fibers with relatively large diameters, and these fibers age more rapidly than fibers with smaller diameters, which are part of the parvocellular system. With the stimuli of the prior art, it is difficult and very time-consuming to detect magnocellular systems. As mentioned above, however, this capability would be very desirable for the early detection of glaucoma.

SUMMARY OF THE INVENTION

The object of the invention is to create a stimulus and a method for the early detection of glaucoma, among other disorders, which makes a more rapid and more reliable test method possible. The method is a method for measuring or testing the perimetry of the field of vision.

The invention teaches a stimulus of the general type described above that has at least two visual characteristics that can be varied for the determination of the threshold. The stimulus claimed by the invention makes possible a test method in which the stimulus can be varied from one test site to another in terms of two characteristics. These two characteristics include, but are not limited to, contrast and resolution. The variation of two characteristics makes possible a more reliable, more rapid and selective detection of magnocellular fibers.

In one embodiment of the invention, a stimulus of the type described above is formed by sine waves. These waves preferably form wave crests and wave troughs that are moved radially outward from a center. The appearance of a stimulus of this type resembles the surface of a liquid after the impact of a drop of fluid on the surface. Radially outward, toward the periphery, the amplitude of the waves becomes smaller and approaches the background. The two characteristics that can be easily and precisely varied with such a stimulus are the amplitude and the distance between the wave crests and the wave troughs. However, the waves can also be moved outward more rapidly or more slowly. Finally, it is also possible to vary the color. Subsequent stimuli can therefore be differentiated in particular with reference to their contrast and/or their resolution. For example, in the presentation of an additional stimulus, the contrast or the resolution can be varied. It is also possible, however, to vary the contrast and the resolution simultaneously. Different cellular systems respond differently to such variations. Such different functions can be diagnosed using the stimuli claimed by the invention.

The method claimed by the invention is characterized by the fact that the stimulus is varied in terms of two visual characteristics during one test. The method is therefore based on the teaching that the stimulus is varied from one test site to another not only in terms of one characteristic, but also in terms of two characteristics. These characteristics are preferably contrast and resolution. An additional characteristic is the speed of movement, for example, the speed at which a wave is moved radially outward from a center. Therefore in one additional conceivable realization, the stimulus is varied with regard to more than two characteristics. With an unchanging luminance, for example, the contrast and/or the resolution and/or the speed of movement can be varied to determine a threshold.

BRIEF DESCRIPTION OF THE DRAWINGS

FIG. 1 is a view of a stimulus according to the invention;

FIG. 2 is a schematic diagram of the wave-shaped structure of a stimulus; and

FIG. 3 is a diagram of a plurality of stimuli that are different with respect to their contrast and their spatial resolution.

DESCRIPTION OF THE PREFERRED EMBODIMENTS

The stimulus 1 illustrated in FIGS. 1 and 2 is presented in predetermined test sites on a perimeter which is itself a device of the prior art. Such methods are well-known to a technician skilled in the art.

The stimulus 1 forms a region of background 2 which is presented on a screen, for example. It consists of ring-shaped wave crests 4 and wave troughs 5, which are concentric to a center 3. The wave crests 4 appear darker than the background 2, while the wave troughs 5 are brighter than the background 2. The transition from the wave crests 4 to the wave troughs 5 is preferably a sine wave, as shown in FIG. 2. The wave crests 4 and the wave troughs 5 extend radially outward from the center 3, similar to the case with waves that are generated by a drop falling on the surface of water. The amplitude is greatest in the center 3 and decreases toward the periphery, as shown in FIG. 2. The luminance finally fades into the background at the periphery. This background 2 is preferably illuminated uniformly.

During a presentation, the characteristics of the stimulus 1 are preferably constant. The stimulus 1 therefore has a defined luminance and a defined contrast, as well as a defined resolution. It is also possible, however, to have a realization in which at least one of these characteristics is varied during the presentation. For example, the contrast can be varied during the presentation of the stimulus 1. These characteristics are preferably not varied during the presentation, but from one stimulus to the next. FIG. 3 illustrates an example of a plurality of stimuli 0 to 35 that are presented sequentially during a test and differ in terms of contrast and/or resolution. The stimulus 0 has a maximum contrast of 100% and a high resolution. A stimulus 1 of this type is visually easy to recognize. The wave crests 4 with such a stimulus in the center are essentially black, while the wave troughs 5 are white. For the subsequent stimulus 1, which can be presented at another test site, the contrast is less, and in this case is 89%. The spatial resolution is the same as for the stimulus 0. The stimulus 2, in turn, has a reduced contrast. The subsequent stimulus 3 differs from the stimulus 2 in terms of a higher resolution with the same contrast. In the test, the contrast and the resolution are thus varied in steps, so that ultimately a stimulus 35 can be presented that has a very low contrast and high resolution. The values are conventionally indicated in decibels.

The rings formed by the wave crests 4 and wave troughs 5 are preferably circular. However, these rings can also have another shape. For example, they can be polygonal or oval. The number of these rings or wave crests 4 and wave troughs 5 can also be different. Preferably, however, there is a plurality of wave crests 4 and wave troughs 5.

The total luminance of the stimulus 1 is preferably the same as the luminance of the background 2. This situation is immediately apparent, for example, in the illustration presented in FIG. 2. This total luminance is preserved even if the contrast or the luminance or the speed of movement is varied. When the contrast is increased, therefore, the wave crests 4 become darker and the wave troughs 5 brighter. Basically, however, a method is possible in which the total luminance is lesser or greater than the luminance of the background 2. For example, a method is conceivable in which the subsequent stimuli differ only in terms of the luminance of the wave troughs 5, whereby the luminance of the background 2 remains constant. The total luminance of the stimulus 1 can thus differ from the luminance of the background 2. An essential characteristic of the stimulus 1 is, therefore, its variation with respect to at least two characteristics. Thresholds can therefore be determined not only with reference to the luminance, but in particular also with reference to the contrast and the resolution, as well as with regard to the speed of movement. A threshold can thereby be determined by variations of the contrast and the resolution.

What is claimed is:

1. A stimulus for testing a field of vision of a human eye which is presented as a region of a background of a perimeter to a test subject at predetermined test sites, wherein the stimulus has at least two characteristics that can be varied for determination of a threshold, wherein the stimulus is formed by waves and wherein the waves expand coaxially from a center toward a periphery.

2. The stimulus as claimed in claim 1, wherein the stimulus is formed by sine waves.

3. The stimulus as claimed in claim 2, wherein the sine waves expand coaxially from a center toward a periphery.

4. The stimulus as claimed in claim 3, wherein the stimulus has ring-shaped wave crests and wave troughs, the amplitude of which becomes smaller toward the periphery.

5. The stimulus as claimed in claim 4, wherein the wave crests and wave troughs move, and wherein the speed of movement is variable.

6. The stimulus as claimed in claim 5, wherein the wave crests and wave troughs move radially outward from a center.

7. The stimulus as claimed in claim 1, wherein the total luminance of the stimulus is essentially equal to the luminance of the background.

8. The stimulus as claimed in claim 1, wherein one visual characteristic is contrast and another visual characteristic is resolution.

9. A method for testing a field of vision of a human eye consisting of presenting a stimulus in predetermined test positions to a test subject, wherein the stimulus has at least two characteristics that are varied during the test for determination of a threshold, wherein the stimulus is formed by waves and wherein these waves expand coaxially from a center toward a periphery.

10. The method as claimed in claim 9, wherein the stimulus is presented with differing contrast in different regions.

11. The method as claimed in claim 9, wherein the stimulus is presented with differing resolution in different regions.

* * * * *